US00PP14155P39

(12) United States Plant Patent
Noodelijk

(10) Patent No.: US PP14,155 P3
(45) Date of Patent: Sep. 23, 2003

(54) CHRYSANTHEMUM PLANT NAMED 'SCOTT'

(75) Inventor: Robert Noodelijk, Woubrugge (NL)

(73) Assignee: Chrysanthemum Breeders Association NV (NL)

( * ) Notice: Subject to any disclaimer, the term of this patent is extended or adjusted under 35 U.S.C. 154(b) by 0 days.

(21) Appl. No.: 09/923,392

(22) Filed: Aug. 8, 2001

(65) Prior Publication Data

US 2003/0074706 P1 Apr. 17, 2003

(51) Int. Cl.[7] ..... A01H 5/00

(52) U.S. Cl. ..... Plt./286

(58) Field of Search ..... Plt./286

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A Chrysanthemum plant named 'Scott' characterized by its medium sized blooms with purple ray-florets and yellow disc florets.

2 Drawing Sheets

BACKGROUND OF THE INVENTION

'Scott' is a product of a breeding-program that had the objective of creating new chrysanthemum cultivars with a daisy type flower, a 7 week response and a medium plant height. The new plant of the present invention comprises a new and distinct cultivar of Chrysanthemum plant. 'Scott' is a seedling from a cross in a breeding program maintained under the control of inventor. The female and male parents are unknown, originating from a mixed population of crossing parents. The new and distinct cultivar was discovered and selected as a flowering plant within the progeny of the stated cross by Rob Noodelijk in a controlled environment (greenhouse) in Rijsenhout, Holland in August, 1998. The first act of asexual reproduction of 'Scott' was accomplished when vegetative cuttings were taken from the initial selection in October, 1998 in a controlled environment in Rijsenhout, Holland.

SUMMARY OF THE INVENTION

The present invention is a new and distinct variety of chrysanthemum bearing medium sized blooms with purple ray-florets and yellow disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
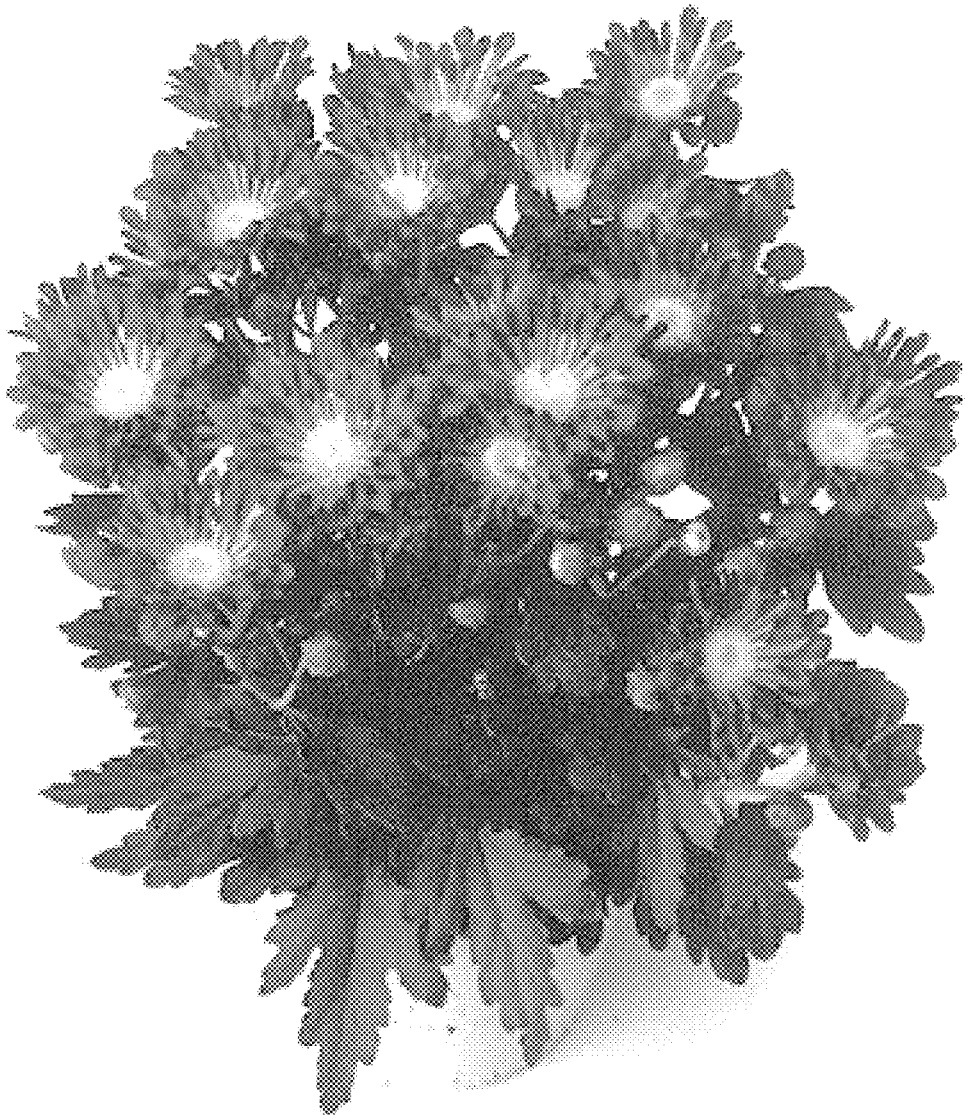
FIG. 1 shows a plant of the cultivar in full bloom.
Figure 2:
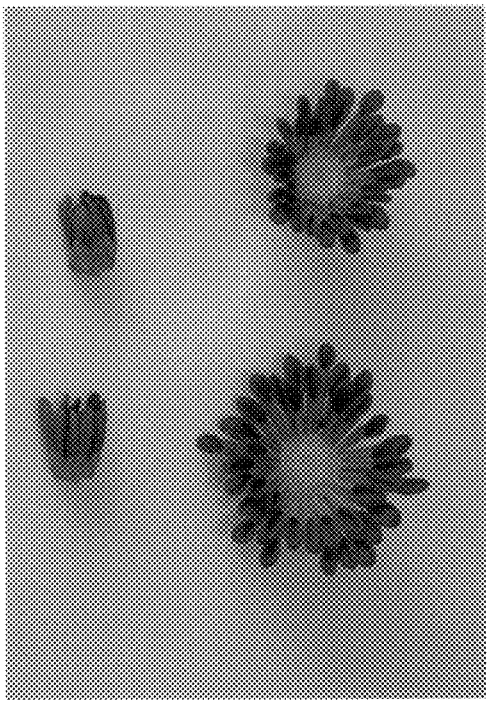
FIG. 2 shows the various stages of bloom of the new cultivar.
Figure 3:
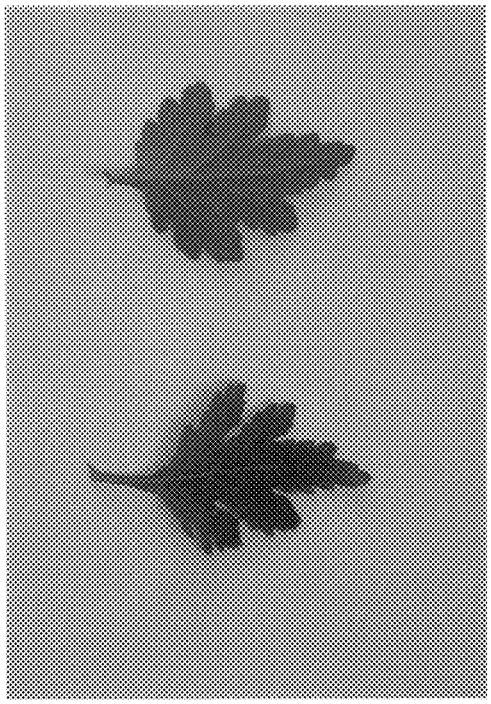
FIG. 3 shows the foliage of the new cultivar.

This new variety of chrysanthemum is of the botanical classification *Chrysanthemym morifolium*. The observations and measurements were gathered from plants grown in a greenhouse in Rijsenhout, Holland in a photo-periodic controlled crop under conditions generally used in commercial practice. The greenhouse temperatures during this crop were at day-time between 18° C. and 25° C. and at night 20° C.

The photo-periodic response time in this crop was 50 days after an average of eight long days. After this long day period to flowering, growth retardants were applied 6 times in an average dose of 1.5 gram/liter water. No tests were done on disease or insect resistance or susceptibility. This new variety produces medium sized blooms with purple ray-florets and yellow disc-florets blooming on the plant for 5 weeks. This new variety of chrysanthemum has been found to retain its distinctive characteristics throughout successive propagations; however, the phenotype may vary significantly with variations in environment such as light intensity and temperature. To show the phenotype as described, 'Scott' can be planted without assimilation lightning (high pressure sodium lamps) between week 50 and week 40 of the next year under greenhouse conditions in Holland. With assimilation lightning (minimum level 2500 lux) it can be planted year round under greenhouse conditions in Holland.

From the cultivars known to inventor the most similar existing cultivar in comparison to 'Scott' is 'Rapture'. 'Scott' and 'Rapture' has a same type of daisy flower with spoontype ray-florets. When 'Rapture' and 'Scott' are being compared the following differences are noticed: The differences of 'Rapture' and 'Scott' are: (1) Flower color. The purple color of 'Scott' is darker. (2) Response time. The response time of 'Scott' is shorter. (3) Color of the disc florets. Center of the flower of 'Scott' is more yellow.

The following is a description of the plant and characteristics that distinguish 'Scott' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, 1995 edition.

Table 1: Botanical Description of cultivar 'Scott'

Bud:

*Size.*—Medium; cross-section 1.0 cm, height 1.3 cm
*Outside color.*—Red-purple 59 C. .

*Involucral bracts.*—2 rows, length 7 mm, width 3 mm.
*Involucral bracts among disc-florets.*—Not present.
*Involucral bracts color.*—Green 138 A.

Bloom:
*Type.*—Daisy.
*Height.*—Flat.
*Size.*—Medium.
*Fully expanded.*—5.0–6.0 cm.
*Number of blooms per branch.*—Approx. 4 blooms per branch.
*Performance on the plant.*—5 weeks.
*Seeds.*—Produced in small quantities, oval shaped, grey-brown 199 A, 1.5 mm in length.
*Fragrance.*—Typical chrysanthemum.

Color:
*Center of the flower* (*disc-florets*).—Immature a dot of yellow-green 144 A, most is yellow-green 151 A. Mature yellow-green 151 A.
*Color of upper surface of the majority of the ray-florets.*—Red-purple 60 A.
*Color of the lower surface of the majority of the ray-florets.*—Red-purple 64 C.
*Tonality from distance.*—A pot mum with purple spoon type flower.
*Discoloration to color.*—None.

Ray florets:
*Texture.*—Upper and under side smooth.
*Number.*—39–41.
*Cross-section.*—Tubular.
*Longitudinal axis of majority.*—Straight.
*Length of corolla tube.*—Long (1.5 cm.).
*Ray-floret length.*—2.5 cm.
*Ray-floret width.*—0.3 cm.
*Ratio length/width.*—High.
*Shape of tip.*—Spatulate.

Disc florets:
*Disc diameter.*—1.5 cm.
*Distribution of disc florets.*—Numerous and clearly visible at all stages of flowering.
*Shape.*—Tubular.
*Color.*—Yellow-green 151 C.
*Receptacle shape.*—Conical raised.

Reproductive organs:
*Stamen* (*present in disc florets only*).—Thin, 4 mm. length.
*Stamen color.*—Yellow-green 151 C.
*Pollen.*—Present.
*Pollen color.*—Yellow 12 A.
*Styles* (*present in both ray and disc florets*).—Thin.
*Style color.*—Yellow-green 144 C.
*Style length.*—5 mm.
*Stigma color.*—Yellow-green 144 C.
*Stigma width.*—1 mm.
*Ovaries.*—Enclosed in calyx.

Plant:
*Form.*—A pot mum meant for indoor use.
*Growth habit.*—Spreading.
*Growth rate.*—Rapid.
*Height.*—28.0–31.0 cm.
*Width.*—27.0 cm.
*Stem color.*—Green 138 A.
*Stem strength.*—Medium.
*Stem brittleness.*—Absent.
*Stem anthocyanin coloration.*—Present with a thin layer of Greyed-red 178 B.
*Length of lateral branch.*—From top to bottom 14.0 cm.
*Lateral branch color.*—Green 138 A.
*Lateral branch, attachment.*—Weak.
*Branching* (*average number of lateral branches*).—Good with 5 breaks after pinching.
*Peduncle length.*—2.0–3.0 cm.
*Peduncle color.*—Green 138 A.
*Flowering response* (*photo-periodic controlled crop, not natural season*).—50 Days.

Foliage:
*Color.*—Upper side green 137 A. Under side green 138 A.
*Size.*—Small; length 7.0 cm, width 4.0 cm.
*Quantity* (*number per lateral branch*).—5–6.
*Shape.*—Oval.
*Texture upper side.*—Glabrous.
*Texture under side.*—Pubescent.
*Ribs and veins upper side.*—Ribs and veins well developed.
*Ribs and veins upper side.*—Ribs and veins well developed.
*Venation arrangement.*—Palmate.
*Shape of the margin.*—Serrated.
*Shape of base of sinus between lateral lobes.*—Acute.
*Margin of sinus between lateral lobes.*—Converging.
*Shape of base.*—Asymmetric.
*Apex.*—Cuspidate.

Differences with the comparison varieties

| | 'SCOTT' | 'RAPTURE' |
|---|---|---|
| Color of ray-florets | Red-purple 60 A | Red-purple 61 B |
| Color of disc-florets | Yellow-green 151 A | Yellow-green 144 A |
| Response time | 50 days | 56 days |

I claim:

1. A new and distinct variety of chrysanthemum plant as described and illustrated.

* * * * *